(12) United States Patent
Brushwyler

(10) Patent No.: US 7,488,106 B2
(45) Date of Patent: Feb. 10, 2009

(54) AUTOMATED CALORIMETER

(75) Inventor: Kevin R. Brushwyler, St. Joseph, MI (US)

(73) Assignee: Leco Corporation, St. Joseph, MI (US)

( * ) Notice: Subject to any disclaimer, the term of this patent is extended or adjusted under 35 U.S.C. 154(b) by 233 days.

(21) Appl. No.: 11/416,970

(22) Filed: May 3, 2006

(65) Prior Publication Data

US 2006/0251145 A1 Nov. 9, 2006

Related U.S. Application Data

(60) Provisional application No. 60/677,988, filed on May 5, 2005.

(51) Int. Cl.
*G01K 17/00* (2006.01)
*G01N 25/20* (2006.01)

(52) U.S. Cl. .............................. 374/33; 374/31; 374/36; 422/51; 436/137

(58) Field of Classification Search ............. 374/31–42, 374/43, 138, 144, 157, E17.001, E17.004, 374/E17.006; 436/147; 422/50, 51; 236/12.13
See application file for complete search history.

(56) References Cited

U.S. PATENT DOCUMENTS

| | | | |
|---|---|---|---|
| 550,943 A | 12/1895 | Carpenter | |
| 1,103,915 A | 7/1914 | Junkers | |
| 1,247,998 A | 11/1917 | Parr | |
| 2,141,453 A | 12/1938 | Schmidt | |
| 2,349,517 A | 5/1944 | Pinkerton | |
| 3,285,053 A | 11/1966 | Mazieres | |
| 3,456,490 A | 7/1969 | Stone | |
| 3,593,577 A | 7/1971 | Monner | |
| 3,599,666 A | 8/1971 | Curtis et al. | |
| 3,650,306 A | 3/1972 | Lancaster | |

(Continued)

FOREIGN PATENT DOCUMENTS

CH        571218        12/1975

(Continued)

OTHER PUBLICATIONS

Koehler Instruments Model K88800☐☐http://web.archive.org/web/20061104094452/http://www.koehlerinstrument.com/products/K88800.html☐☐Published date: Nov. 4, 2006.*

(Continued)

*Primary Examiner*—Edward Lefkowitz
*Assistant Examiner*—Bret Adams
(74) *Attorney, Agent, or Firm*—Price, Heneveld, Cooper, DeWitt & Litton, LLP

(57) ABSTRACT

An automated apparatus for determining the calorific value of combustible substances employs an integrated, isothermal water reservoir to reduce the complexity of the apparatus and facilitates automation of the calorimeter by providing a convenient source of isothermal water. A moving divider is used to reconfigure the isothermal water reservoir to either provide for temperature equilibration prior to sample analysis or define a fixed volume of water during analysis in which high precision temperature measurements can be recorded. The apparatus includes mechanisms for controlling the moving divider, a sample holding combustion vessel, and loading, cleaning, and unloading the combustion vessel. This eliminates key analysis steps that had previously required manual intervention by an operator.

25 Claims, 14 Drawing Sheets

U.S. PATENT DOCUMENTS

| | | | | |
|---|---|---|---|---|
| 3,665,761 | A | * | 5/1972 | Gregory ........................ 374/31 |
| 3,789,662 | A | | 2/1974 | Zettler et al. |
| 3,978,325 | A | | 8/1976 | Goldstein et al. |
| 4,398,836 | A | | 8/1983 | Sitek |
| 4,511,263 | A | | 4/1985 | Prosen |
| 4,616,938 | A | | 10/1986 | Bonnard |
| 4,816,730 | A | * | 3/1989 | Wilhelm et al. ......... 318/568.22 |
| 4,846,584 | A | * | 7/1989 | Burch et al. ................... 374/31 |
| 4,859,077 | A | * | 8/1989 | Ito et al. ........................ 374/33 |
| 4,923,306 | A | * | 5/1990 | Fauske ......................... 374/34 |
| 4,925,315 | A | * | 5/1990 | Bonnard ....................... 374/31 |
| 5,322,360 | A | * | 6/1994 | Willis et al. .................. 374/38 |
| 5,819,508 | A | * | 10/1998 | Kraft et al. ..................... 53/492 |
| 6,089,124 | A | * | 7/2000 | Murphy ......................... 81/3.39 |
| 6,203,760 | B1 | * | 3/2001 | van der Plaats et al. ...... 422/104 |
| 6,627,451 | B2 | * | 9/2003 | Pinhack et al. .............. 436/147 |
| 6,860,632 | B2 | * | 3/2005 | Groeschner ................... 374/12 |
| 2002/0176799 | A1 | * | 11/2002 | McCorkle ..................... 422/64 |
| 2004/0241864 | A1 | * | 12/2004 | Sattler et al. .................. 436/43 |

FOREIGN PATENT DOCUMENTS

| | | |
|---|---|---|
| DE | 238395 | 5/1910 |
| DE | 2840595 | 9/1978 |

OTHER PUBLICATIONS

Perkin Elmer Jade DSC http://las.perkinelmer.com/content/RelatedMaterials/Brochures/BRO_JadeDSCDiffScanningCalorimeter.pdf No publication date. First visited Apr. 23, 2008.*

U-Therm Inc Model JingYing http://www.u-therm.net/productdetail.aspx?id=36 No publication date. First visited Apr. 23, 2008.*

* cited by examiner

AUTOMATED CALORIMETER

CROSS-REFERENCE TO RELATED APPLICATIONS

This application claims priority under 35 U.S.C. § 119(e) on U.S. Provisional Application No. 60/677,988 entitled AUTOMATED CALORIMETER, filed on May 5, 2005, by Kevin R. Brushwyler, the entire disclosure of which is incorporated herein by reference.

BACKGROUND OF THE INVENTION

The present invention relates to a calorimeter including a combustion vessel and an integrated isothermal fluid reservoir.

A somewhat complicated apparatus has been employed for the determination of the calorific value of solid and liquid substances in accordance with standard methodology (ASTM/ISO documents). The operation of such an apparatus is well understood and has been described in, for example, the American National Standard Institute ANSI/ASTM D5865.

Prior calorimeters have required the use of multiple internal and external reservoirs with which to contain and manage the water required to operate the apparatus. U.S. Pat. Nos. 4,398,836 and 4,616,938 disclose calorimeters which have a tank for holding a calorimeter combustion vessel and a separate water tank coupled by conduits and valves for supplying water to the vessel. In another calorimeter disclosed in U.S. Pat. No. 4,616,938, two distinct reservoirs were employed, including an internal jacket reservoir and a permanent internal bucket reservoir. In another calorimeter disclosed in U.S. Pat. No. 5,322,360, four distinct water reservoirs are employed:

1) A first internal reservoir, commonly referred to as a jacket, is employed to provide a constant isothermal environment.
2) A second internal reservoir is employed to provide a ballast volume of water from which to fill an external burette.
3) A third external reservoir, commonly referred to as a burette, is employed to deliver a reproducible amount of analysis water.
4) A fourth transportable reservoir, commonly referred to as a bucket, is used to receive the water delivered from the burette and to contain the combustion vessel. The bucket is installed in the analyzer and temperature measurements of the bucket are recorded during the course of the analysis.

One disadvantage of using separate reservoirs in a calorimeter is that, during routine operation, the systems require an external source of coolant water to eliminate thermal energy generated by the combustion of the sample. Also, the use of multiple reservoirs in such prior art systems requires numerous valves and conduits with which to direct the water to and from the reservoirs.

The operation of prior art isothermal calorimeters is further complicated by the requirement to maintain the temperature of the water substantially constant in all reservoirs from one analysis to the next. Additionally, upon the completion of an analysis, any heat resultant from the combustion of the sample must be removed.

Furthermore, prior art designs required the use of a distinctly separate bucket reservoir in order to ensure that the volume of water contained therein be maintained substantially constant from one analysis to the next. This requirement is a result of the fact that any variation in this volume is proportionally related to imprecision in the observed results. Assuming no other source of error, a variation of 1 part in 1000 in the volume of water will limit the precision the apparatus, correspondingly, to 1 part in 1000.

Various instrumental approaches have been used to reduce this source of error. Typically, these approaches employ either a sensor or an overflow port with which to limit the volume of the water. Among other factors, such approaches are dependant either upon the surface tension of the water or the sensitivity and reproducibility of the sensor. In order to eliminate heat resultant from the combustion of the sample, these approaches require that the water in the bucket be substantially drained and refilled before each analysis. In some cases, the bucket and the combustion vessel must be dried by the operator in order to ensure that the correct volume of water is present.

Common practice for operating prior art instruments requires significant manual intervention by the operator and strict care to operate in a reproducible manner consistent with the desired precision and accuracy of the apparatus. Manual removal of the pressurized vessel from the apparatus constitutes a potential hazard if it is mishandled or otherwise accidentally damaged.

Such handling of the combustion vessel may lead to variations in the initial thermal energy state of the calorimeter. Since the measurement of the calorific value of the sample is based upon a differential measurement of the thermal energy of the calorimeter before and after combustion, such errors in the initial energy state reduces the precision of the apparatus.

As such, to reduce the error of measurement, it would be desirable that manual handling of the combustion vessel by the operator is minimized and/or in some manner automated. Also, it would be desirable to retain the combustion vessel inside the instrument where the initial temperature can be controlled by allowing the combustion vessel to be in intimate contact with the isothermal water circulated within a jacket.

SUMMARY OF THE INVENTION

In accordance with the present invention, these desirable goals are achieved using an improved apparatus and method developed for determining the calorific value of combustible substances. The apparatus employs a moving divider, which can be used to partition a single isothermal reservoir into an outer jacket and an internal bucket for receiving the calorimeter vessel. The apparatus requires fewer plumbing components than prior art systems and is amenable to automation. This reduces operator labor and minimizes operator intervention which can result in analysis errors.

In one embodiment of the invention, a calorimeter system including an isothermal reservoir includes a combustion vessel; an outer jacket having a wall, a fluid inlet and an overflow outlet located near an upper end; a system for circulating fluid from said fluid inlet to provide a constant temperature of fluid within said jacket; a thermally insulated member positioned within said jacket in spaced relationship to the wall thereof and having an internal volume therein defining a bucket for receiving a calorimeter combustion vessel, said insulating member having a height less than the height of said jacket such that fluid in said jacket fills said bucket; and a movable closure member selectively coupled to said calorimeter combustion vessel and including a seal engaging said insulated member for sealing said bucket from said jacket during combustion of a sample within said combustion vessel.

In another embodiment of the invention, a fully automated calorimeter including a combustion vessel and an isothermal reservoir for receiving said combustion vessel is provided and includes a combustion vessel with an open top; a closure member for said top of said combustion vessel, wherein said combustion vessel and closure member include interlocking members; an isothermal reservoir including a bucket for receiving said combustion vessel and a surrounding water jacket having water therein controlled to a predetermined temperature; an arm coupled to said cover for said combustion vessel for lifting said combustion vessel and said cover when said combustion vessel and cover are locked together to a first position in which an upper end of said combustion vessel and said cover are withdrawn from said bucket with a lower end of said combustion vessel held in thermal contact with said water jacket; a gripper assembly including arms for engaging said combustion vessel when in said first position for holding the combustion vessel in said first position and against rotation; rotary actuator means coupled to said cover of said combustion vessel for rotating said cover while said arms of said gripper assembly hold said vessel in a stationary position to disengage the locking members between said cover and said combustion vessel; and wherein said arm is movable to subsequently raise the cover from said combustion vessel to a second position for gaining access thereto and a third lowered position sealing a portion of said isothermal reservoir surrounding said combustion vessel from the remainder of said isothermal reservoir during combustion of a sample. This embodiment contemplates the sequential steps of operation of these structural components.

In yet another embodiment, a method of cleaning a combustion vessel of a calorimeter includes providing a combustion vessel having an open top; providing a source of pressurized air and cleaning fluid; providing a cover for said combustion vessel which includes an inlet check valve and a nozzle with an outlet directed downwardly in said vessel; providing an exhaust, including a mechanically defeatable check valve and a sipper tube, extending through the cover into said vessel, wherein said combustion vessel is cleaned by the admission of pressurized air and cleaning fluid subsequent to combustion, wherein the byproducts of combustion are exhausted from said combustion vessel through said check valve and the cleaning fluid is removed through said sipper tube.

These and other features, objects and advantages of the present invention will become apparent upon reading the following description thereof together with reference to the accompanying drawings.

DETAILED DESCRIPTION OF THE PREFERRED EMBODIMENT

Figure 1:
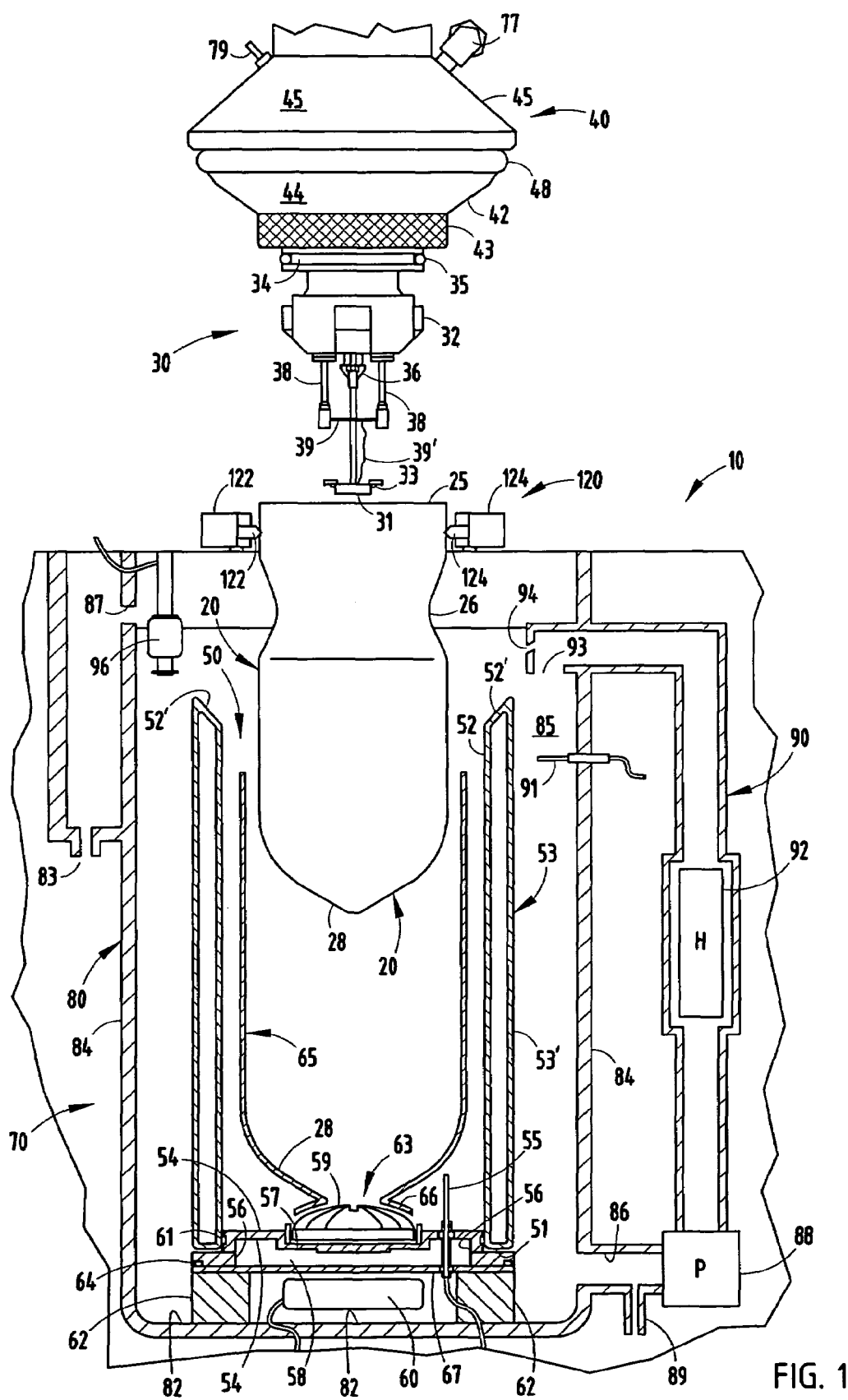
FIG. 1 is an exploded, vertical, partially cross-sectional, view of a calorimeter embodying the present invention, shown with the calorimeter combustion vessel opened.
Figure 2:
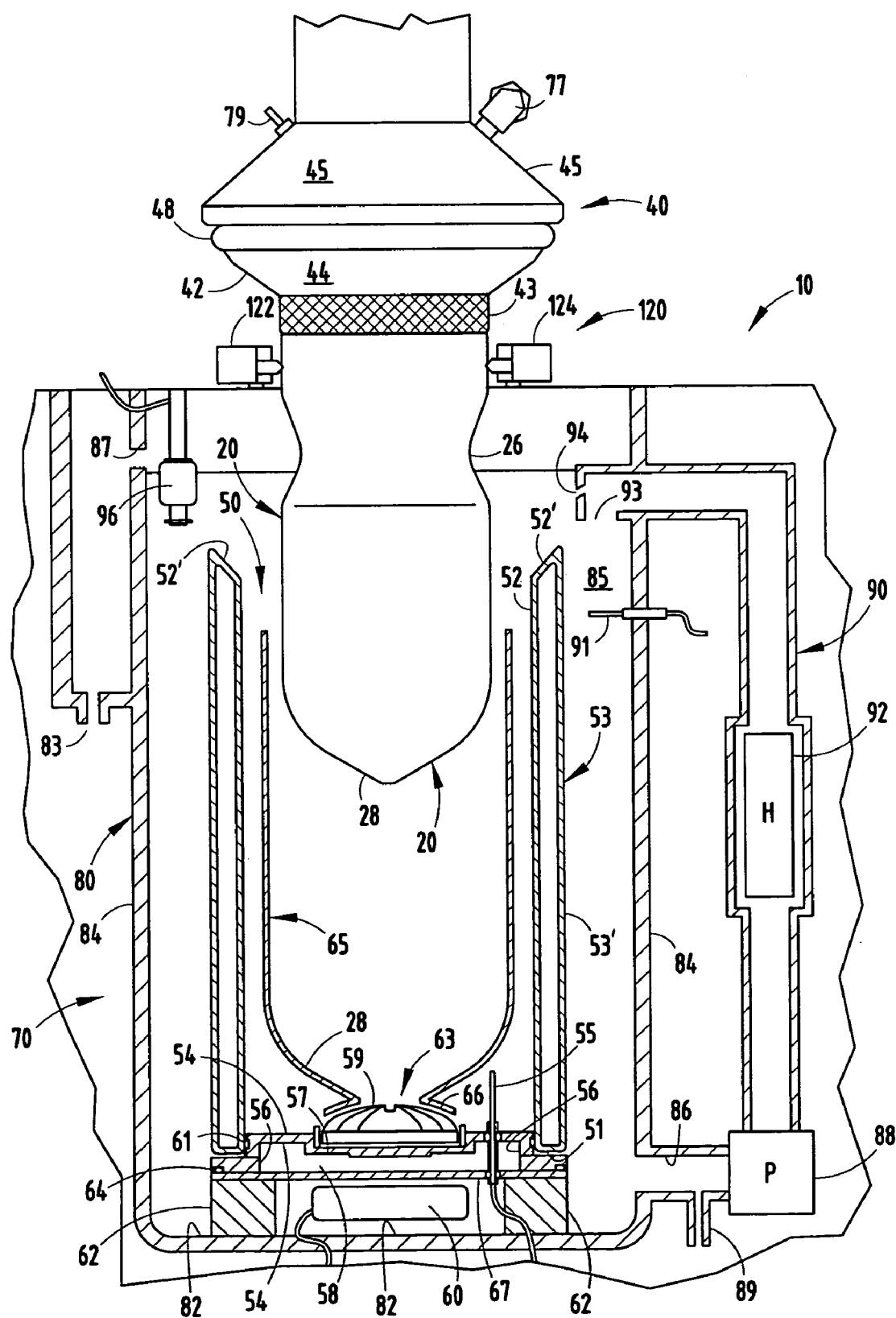
FIG. 2 is an exploded, vertical, partially cross-sectional view of a calorimeter embodying the present invention, shown with the calorimeter combustion vessel closed prior to immersion in the isothermal reservoir.
Figure 3:
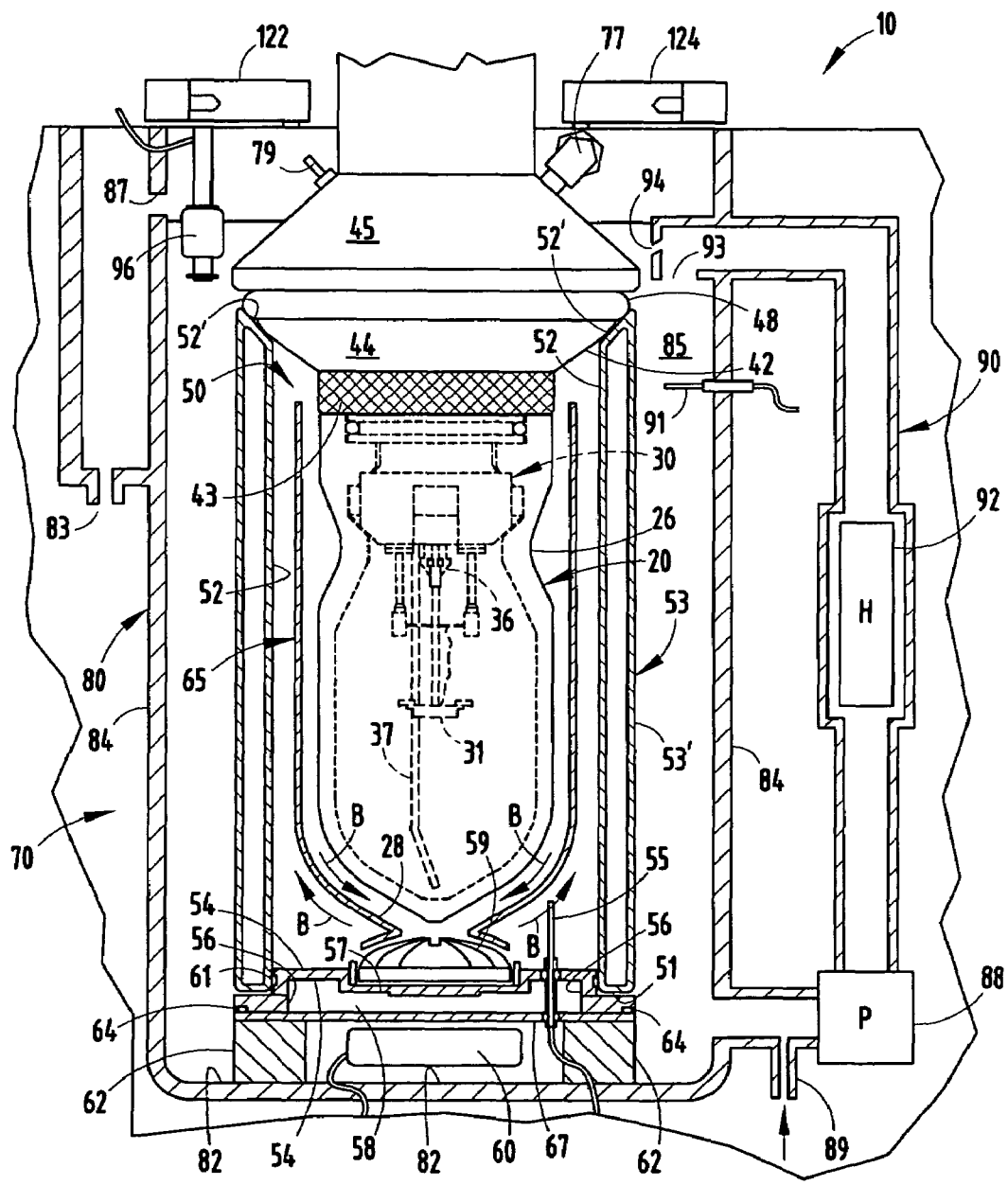
FIG. 3 is a view of the calorimeter, partially in vertical cross section, showing the combustion vessel immersed during an analysis, and partially in phantom, showing the relationship of the combustion vessel and cover.
Figure 4:
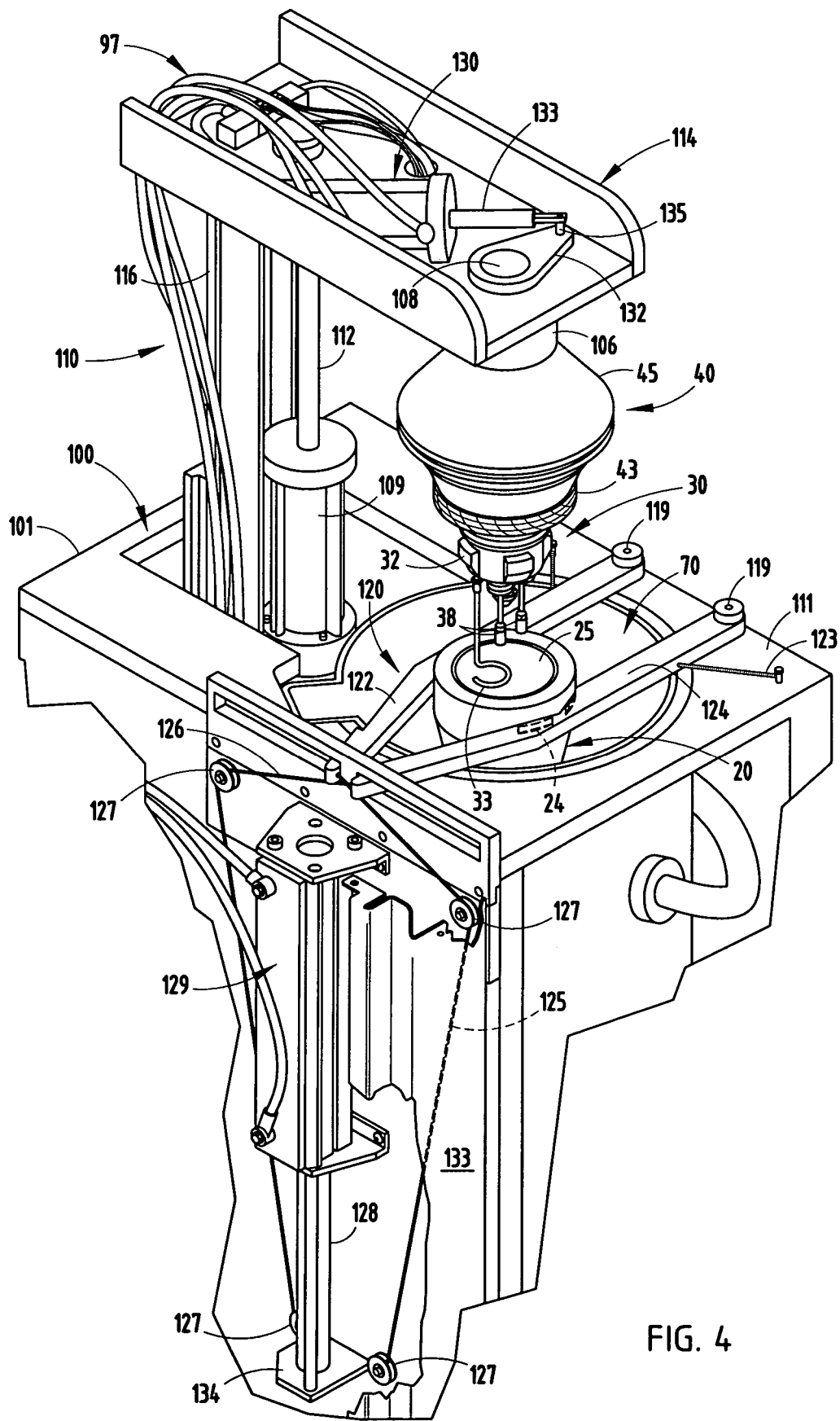
FIG. 4 is a fragmentary perspective view of the calorimeter, shown in an open position and showing the lifting and locking mechanism for the cover and the gripping mechanism for handling the calorimeter vessel.
Figure 5:
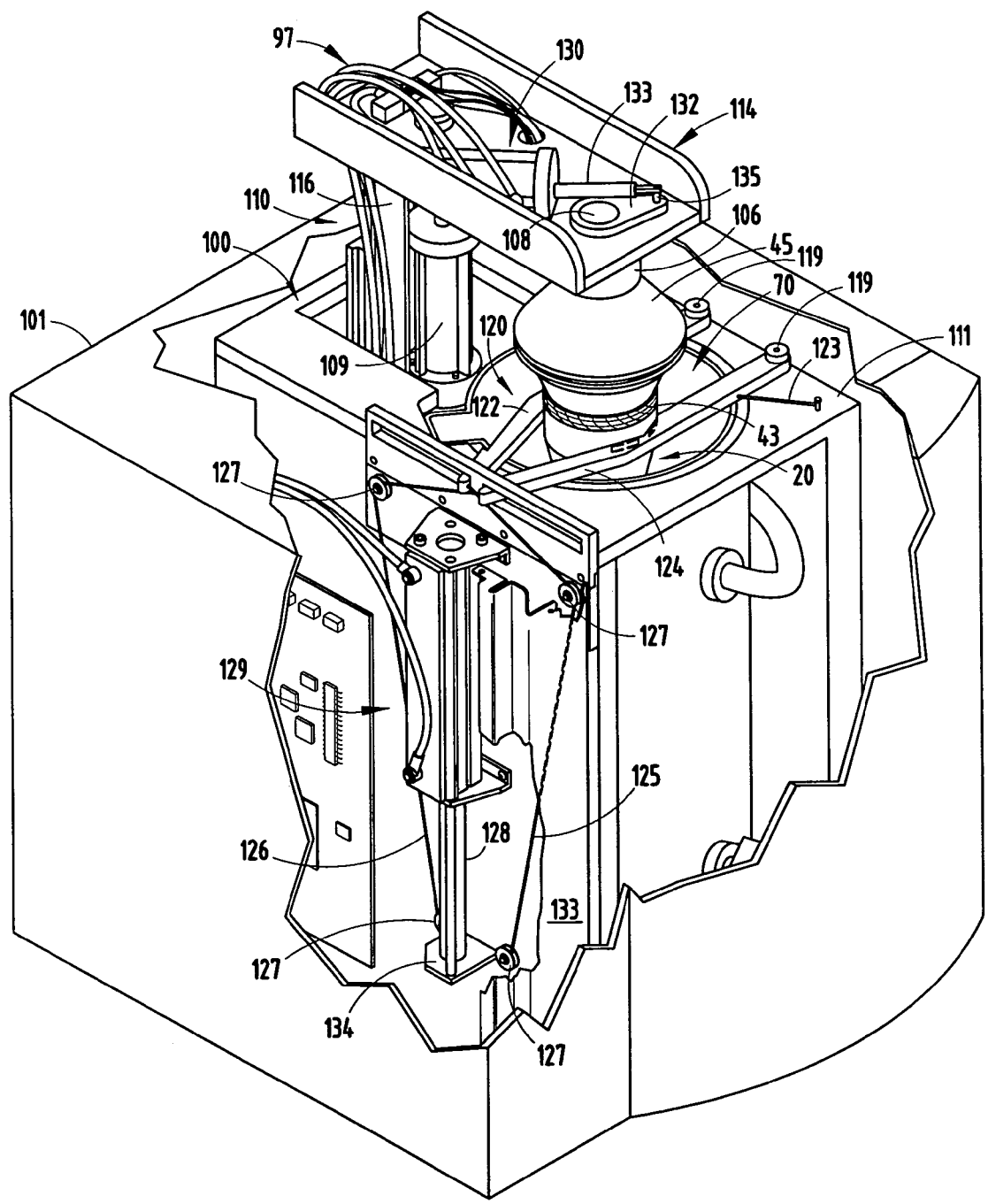
FIG. 5 is an enlarged fragmentary perspective view of the calorimeter shown with the cover in a closed position on the vessel and showing the gripping mechanism in a gripping position for holding the calorimeter vessel when enclosed prior to immersion in the isothermal reservoir.
Figure 6:
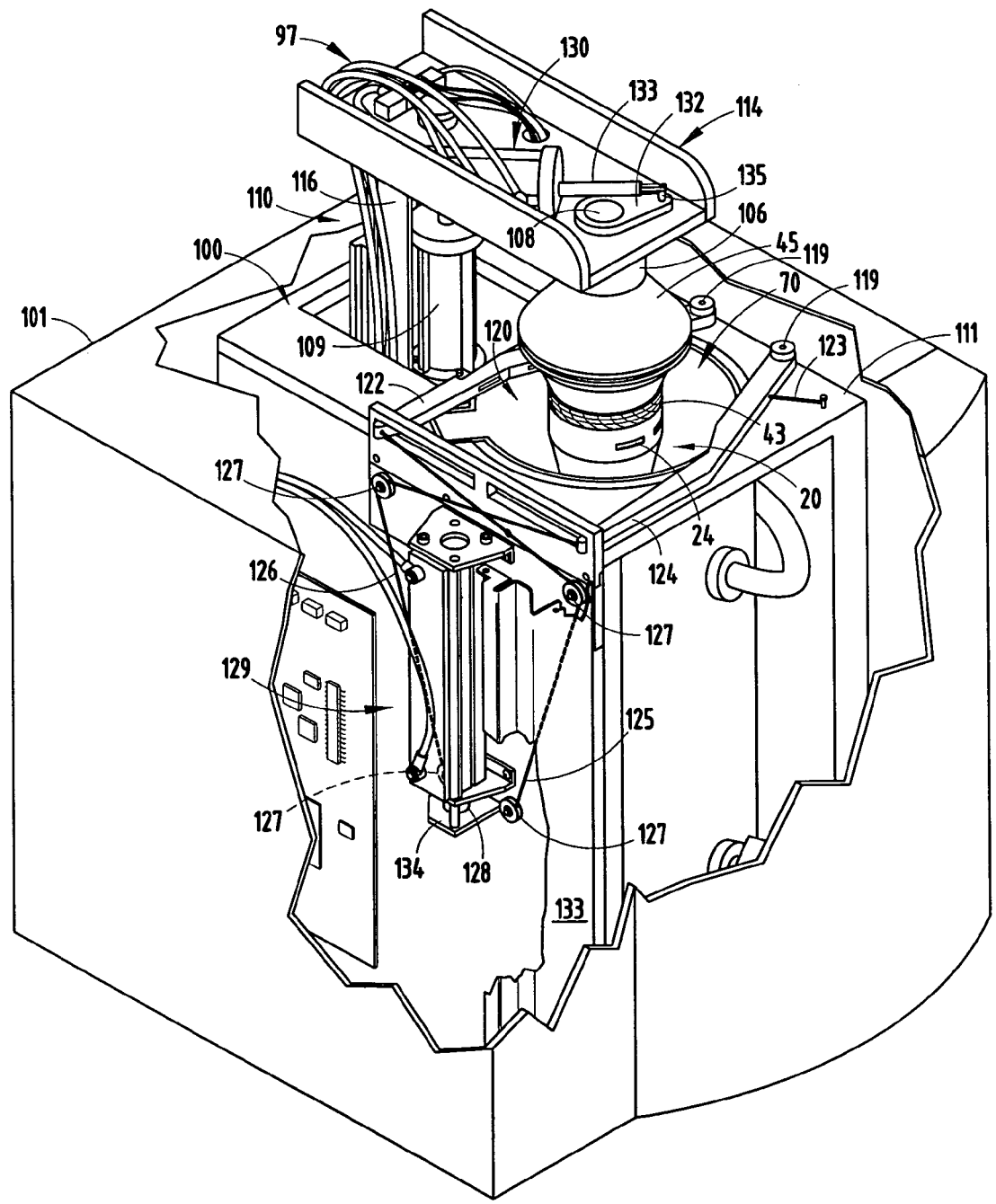
FIG. 6 is an enlarged fragmentary perspective view of the calorimeter with the gripping mechanism shown in a releasing position for allowing the calorimeter vessel to be lowered into the isothermal reservoir.
Figure 7:
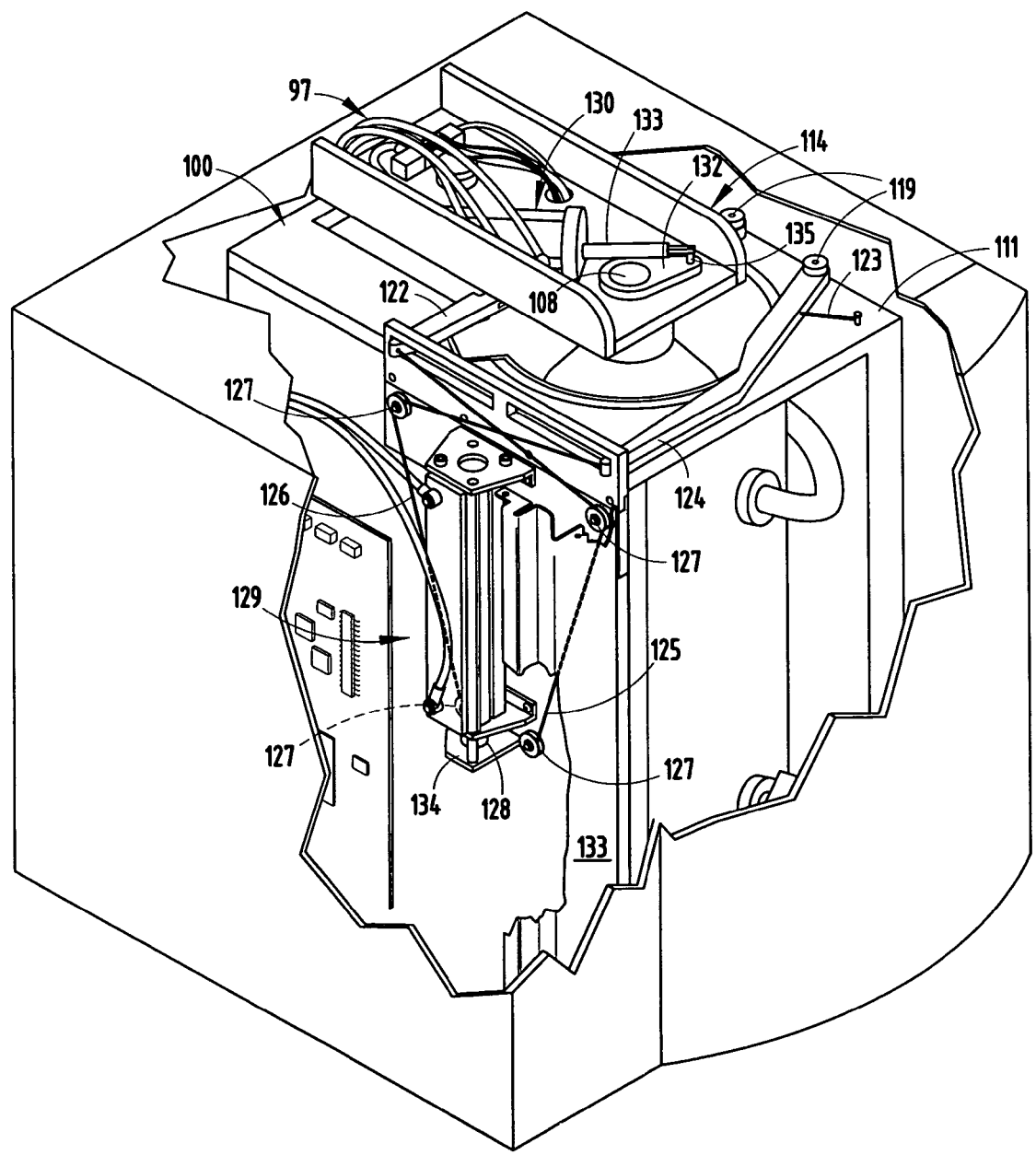
FIG. 7 is a fragmentary perspective view of the calorimeter, showing the divider forming cover assembly lowered to an analysis position for the calorimeter.
Figure 8:
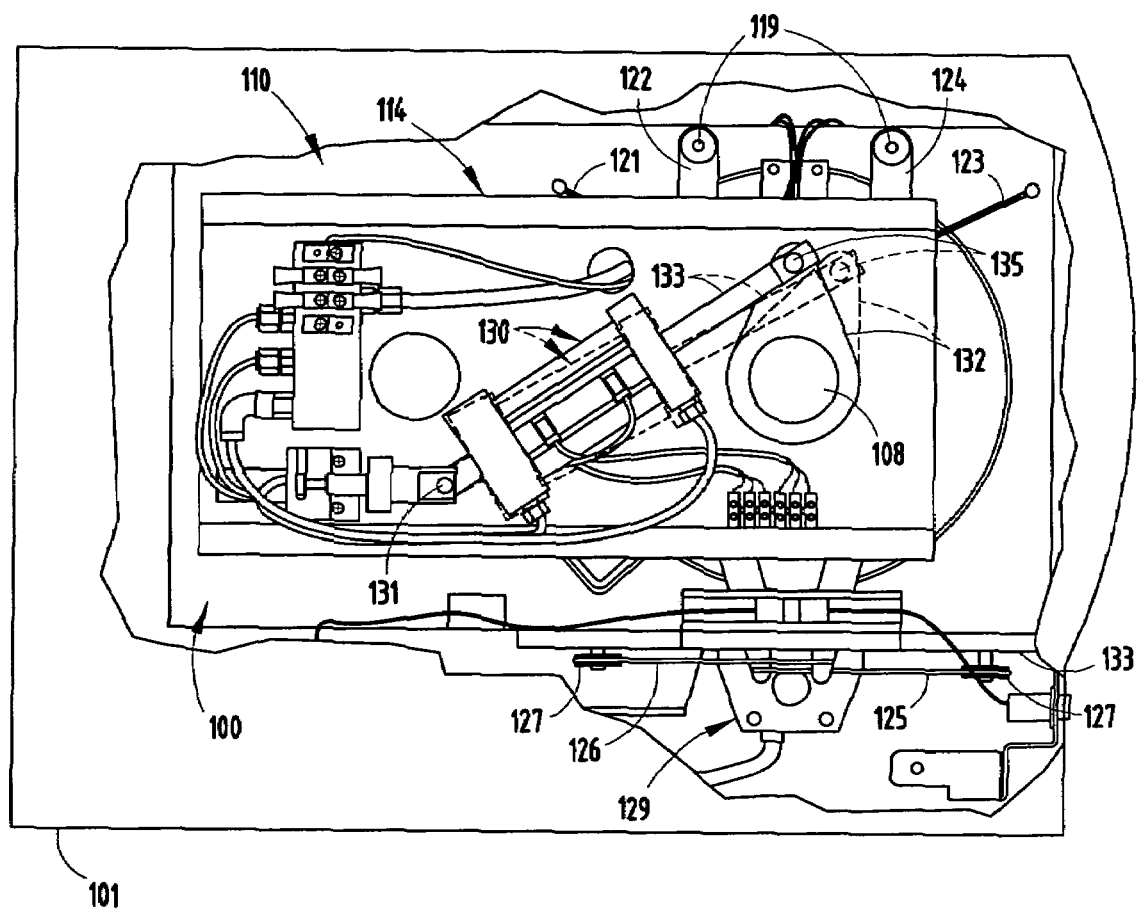
FIG. 8 is a top plan view, partly broken away, of the calorimeter showing the cover locking control and the vessel gripping mechanism.
Figure 9:
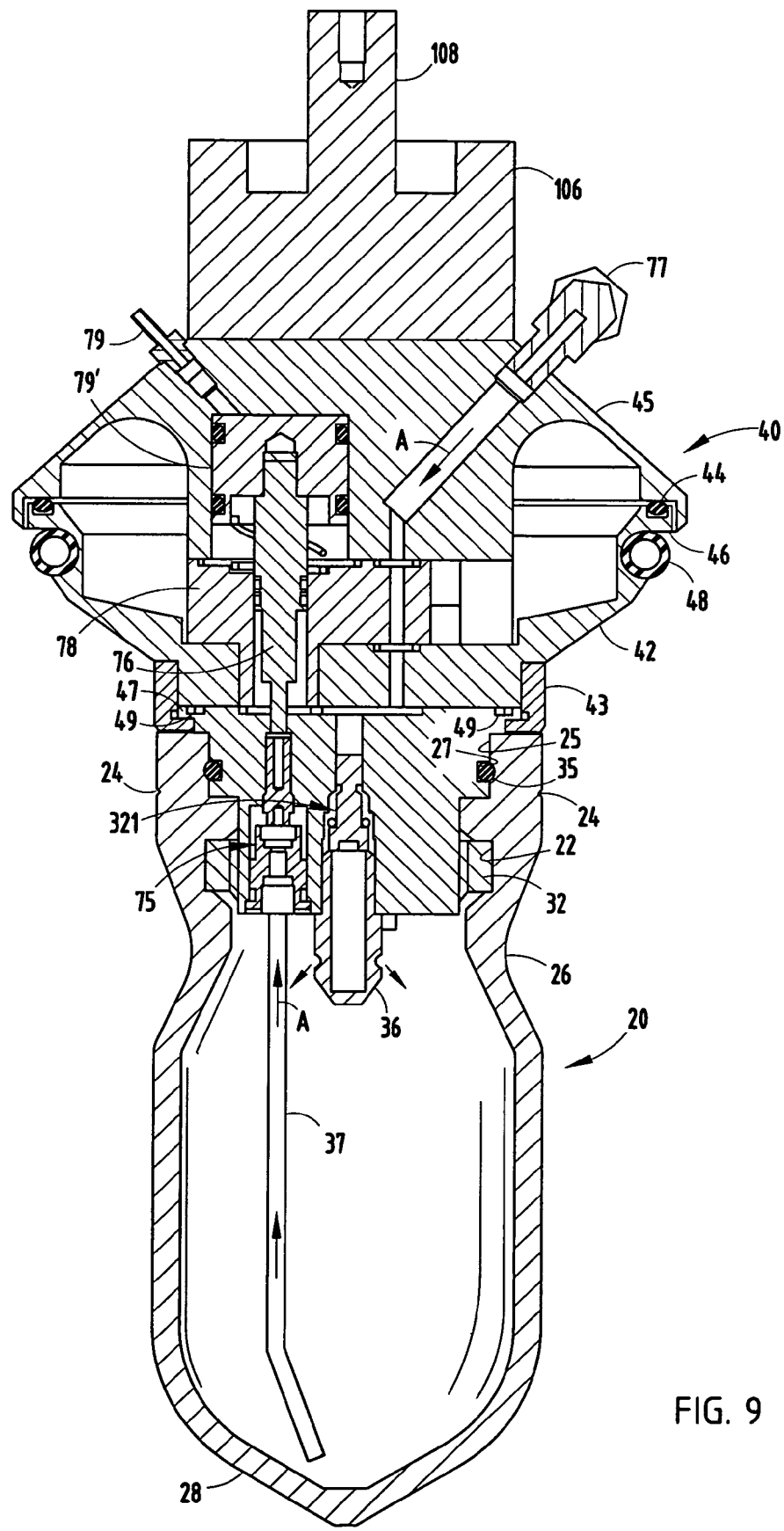
FIG. 9 is an enlarged cross-sectional view of the cover assembly and combustion vessel.

Referring initially to FIGS. 1-7, there is shown a calorimeter 10 embodying the present invention. In FIGS. 1 and 4, the calorimeter is shown in an open position for loading a sample. In FIGS. 2 and 5, the calorimeter is shown in a closed, sealed position prior to immersion in an isothermal reservoir. FIGS. 3 and 7 show the calorimeter in position during an analysis. The calorimeter includes a calorimeter combustion vessel 20, which is made of stainless steel about 0.25 inches thick with an open top 25 and a bullet-shaped curved blunt enclosed lower end 28. Vessel 20 includes internal bayonet threads 22 (best seen in FIG. 9) near the top thereof for lockably receiving external bayonet threads 32 of cover assembly 30 (FIGS. 1, 4, and 9). Vessel 20 also includes a pair of external gripper flats 24 on opposite sides (FIGS. 4-6 and 9) cooperating with the gripping mechanism 120, as described below, to allow the vessel to be held by arms 122, 124 of the gripper mechanism 120, as seen in FIGS. 1, 2, 4, and 5, in a predetermined raised position for rotatably unlocking and locking the cover 30 thereto. The vessel further includes an annular mass reduction groove 26 for reducing the overall thermal mass of the vessel.

Near the open top end 25 of the combustion vessel 20 is an O-ring receiving recess 27 (FIG. 9) which cooperates with an O-ring 35 fitted within an O-ring receiving groove 34 (FIG. 1) of the cover assembly 30 to sealably cover the open top 25 of the combustion vessel 20 when the cover is locked in place during an analysis. The generally cylindrical cover assembly 30 includes a high pressure check valve 321 (FIG. 10) and a coaxial, centrally located nozzle 36 (FIGS. 1, 3, and 9) which is pointed downwardly toward the curved end 28 of the combustion vessel for introducing both pressurized oxygen at 420 psi for pressurizing the vessel prior to the combustion of a sample and also introducing a mixture of a cleaning fluid, such as water, and pressurized air during a cleaning cycle of the combustion vessel 20 as described below.

Cover assembly 30 also includes a sipper tube 37 (FIGS. 3, 9, and 10) which extends from a mechanically defeatable, high pressure check valve in the cover 30 and a gas flow path through top assembly 40 for the exhaust of byproducts of combustion and flushing water and air during the cleaning cycle. The sipper tube 37, as best seen in FIG. 9, has an open lower end which is substantially adjacent the bottom of the curved floor of the combustion vessel and is coupled to an exhaust outlet, such that substantially all water and byproducts of combustion are exhausted from the vessel through a port located in the Kynar® block 78 and exhausted through tubing routed through cover 40 during the cleaning cycle. Check valve 75 is actuated by a pneumatically actuated hammer 76 (FIG. 9) movably and sealably mounted within a Kynar® block 78 secured within the lower section 42 of top assembly 40. A pneumatic fitting 79 coupled to the upper section 45 of top assembly 40 supplies pneumatic pressure to selectively actuate valve 75 as described below.

The cover assembly 30 additionally includes a fuse holder comprising a pair of electrodes 38 (FIGS. 1, 3, and 4) with an electrically heated filament 39 (FIG. 1) mounted therebetween to initiate combustion of the sample via ignition of a cotton string fuse 39'. A sample holding cup 31 retains, for example, a one gram sample to be analyzed (typically an organic material) and is removably held by a sample cup holding ring 33 positioning cup 31 below fuse 39'.

Cover assembly 30 is coupled to the lower section 42 of Teflon® coated aluminum top 40 by a threaded retainer ring 43 having a knurled exterior surface. Ring 43 engages an annular flange 47 on the cover 30 (FIG. 9) to secure the cover to the lower section 42 of top 40. The exterior surfaces of the aluminum top sections 42 and 45 are Teflon® coated to resist corrosion during exposure to water and byproducts of combustion. The aluminum top 40 has excellent thermal characteristics which promote fast equilibration with the water in the isothermal fluid reservoir 70 into which the combustion vessel and lower section 42 of top 40 are immersed. Mechanical contact between the upper cover 45 and the lower cover 42 is minimized to limit the transfer of heat from the bucket 50 to the surrounding isothermal reservoir 70. The top 40 includes conduits extending therethrough, through which the nozzle 36 is supplied oxygen, air, and water and a conduit for the sipper tube 37 and electrical conductors for the heated filament 39. The combustion vessel 20, through its connection with cover 30 and top 40, is raised and lowered into and out of the isothermal reservoir 70 (FIGS. 1-7 and 10) by lift assembly 110 (FIGS. 4-8), which also locks and unlocks the cover assembly 30 between an open position and removed from the combustion vessel 20 (FIG. 4) while vessel 20 is being held by the gripping arms 120, 122 in a closed, lowered position (FIG. 7) for analysis, as described below.

Top 40 includes an upper truncated concave section 45 which is coupled to lift assembly 110 (FIG. 4) by a cylindrical member 106 having an axle 108 which is coupled to a crank arm 132, as described below, for opening and closing vessel 20. Top 40 also includes an inwardly, downwardly tapered lower section 42 which is sealed to upper section 45 by an O-ring seal 44 (FIG. 9) with sections 42 and 45 held together by suitable threaded fasteners 49. The lower section 42 of top 40 includes an annular groove 46 (FIG. 9) near its widest area for receiving a sealing O-ring 48 which, as seen in FIG. 3, sealably engages tapered upper annular surface 52' to seal the closed combustion vessel 20 within a bucket 50 (FIGS. 1-3). Bucket 50 is defined by the inside of cylindrical walls 52 of stainless steel vacuum dewar 53 having an outer wall 53' and annular bottom 51 resting on a floor 54 of the bucket 50. Although the bucket 50 is defined, in part, by the vacuum dewar 53, other cylindrical structures using alternative thermally insulating materials may be employed.

The floor 54 is configured to insulate bucket 50 from the surrounding generally cylindrical jacket 80 of isothermal reservoir 70. For such purpose, the floor includes downwardly and outwardly extending legs 56 which are sealed by O-ring 61 to dewar 53 and O-ring 64 to a support plate 67 spaced by insulating annular pedestal 62 from the floor 82 of jacket 80.

This configuration provides an open, thermally insulating volume 58 between floor 54 of bucket 50 and the floor of jacket 80.

Floor 54 also includes a circular recess 57 for receiving an impeller 59 which extends upwardly from floor 54 and includes an embedded permanent magnet. Impeller 59 is rotated at a speed of about 700 rpm by a rotating magnetic field drive 60 positioned under floor 54 of bucket 50. Impeller 59 is made of a nonferrous metal or a thermoplastic material.

The internal volume of bucket 50 holds approximately 1.5 L (liter) of fluid, typically water, between the lower seal 61 and the upper sealing O-ring 48 which engages the tapered upper edge 52' of dewar 53 when in a closed position, as illustrated in FIGS. 3 and 7. A baffle 65 (FIGS. 1-3), having a shape substantially conforming to that of the combustion vessel 20 but having a diameter slightly greater than the vessel, concentrically surrounds the combustion vessel. Baffle 65 is mounted within bucket 50 by suitable mounting hardware (not shown) in a conventional manner. Baffle 65 has an opening 63 near the bottom thereof and a curved annular wall 66 adjacent and spaced from the impeller 59 for circulating water within the bucket 50 in a direction indicated by arrows B in FIG. 3 during an analysis. Sealably extending through the floor 56 by suitable O-rings is a thermister 55 for measuring the temperature rise of the isothermal fluid (typically water) within the bucket 50 during an analysis sequence.

As best seen in FIGS. 1-3, the bucket 50, including the stainless steel dewar 53, is submerged within a concentric, generally cylindrical jacket 80 having side walls 84 and a bottom 82 with lower outlet port 86 which communicates with a circulatory pump 88. Communicating with the inlet of the pump 88 also is a cold water (fluid) inlet 89. The outlet of pump 88 is coupled by conduit 90 (which integrally includes a heater 92) to a pair of water discharge openings 93 and 94 which introduce water into the jacket volume 85 as well as into the bucket 50 when open and around the exterior of the top section 45 of top 40 when the bucket is sealed. The fluid inlet, pump, and heater can be integrated within the jacket 80 in some embodiments, thereby eliminating the external conduit 90.

Jacket 80, which has an internal volume of approximately 4.5 L, further includes an overflow port 87 which communicates with a drain 83. The level of the water within jacket 80 is controlled by a level indicator 96, which indicates when the water level has reached the level of the overflow port 87. A water jacket temperature sensing thermister 91 is mounted within the wall 84 of jacket 80 to sense the temperature of the water within the jacket and surrounding the stainless steel dewar 53. The water temperature prior to combustion within the jacket volume 85 and in the bucket 50 is held to 25° C.+/−0.001° C., thereby providing an isothermal environment having a volume of 6 L for the submerged combustion vessel prior to combustion. The starting temperature of 25° C. will typically rise in the bucket approximately 3.5° C. during an analysis, while the temperature of the surrounding jacket remains at 25° C. The combination of a slow rate of cold water introduced to inlet 89 through a water manifold 98 (FIG. 10) during an analysis sequence, together with controlling heater 92, assures this precise temperature management of the water within the jacket 80. The jacket tank preferably has walls 84 made of a low thermal conductivity thermoplastic material to facilitate the control of temperature within the jacket surrounding bucket 50.

As seen with reference to FIGS. 4-8, the calorimeter further includes a mechanical frame 100 within a cabinet 101. A lift assembly 110 is mounted to frame 100 and includes a lift cylinder 109 which has a cylinder rod 112 having an end coupled to a horizontally extending arm 114, which has a generally U-shaped cross section. One end of arm 114 is mounted to a vertically extending support pedestal 116 suitably slidably mounted to frame 100. Actuation of cylinder 109, therefore, raises and lowers the top 40 of the combustion vessel (FIG. 1) and, when locked to the combustion vessel 20 itself, also raises and lowers the vessel into and partially from within bucket 50, as illustrated in the position of FIGS. 3 and 7, respectively. When fully raised, the lifting assembly 110 lifts the top 40 and components, including cover 30, form the combustion vessel, as seen in FIGS. 1 and 4.

The opposite end of arm 114 is coupled to the top 40 of the calorimeter 10 by a rotary coupling member 106. The top section 45 also defines a manifold which sealably couples the various conduits through top 40 for supplying oxygen, air, water, and electricity to the combustion vessel. As seen in FIGS. 4-8, conduits, tubes, and hoses 97 for supplying electricity, oxygen, air, and water extend over arm 114 and are coupled through the manifold in upper section 45 of top 40 to the heating element 39, nozzle 36, and sipper tube 37 for the operation of the calorimeter.

The lifting assembly 110 provides the additional function of rotating the top 40 and cover 30 secured thereto for removing the cover from vessel 20 (FIGS. 1 and 4) and locking the cover to vessel 20 (FIGS. 2, 3, and 5-8) while the vessel is held by gripping assembly 120. The combustion vessel is selectively gripped by gripping arms 122, 124, as shown in a gripping position in FIGS. 1, 2, 4 and 5, where gripping arms 122 and 124 compressively engage the gripping flats 24 on the sides of combustion vessel 20. The gripping arms are pivotally mounted by pivot axles 119 (FIGS. 4-8) to the top 111 of frame 100 and are spring-loaded to an open position (FIGS. 6 and 7) by tension springs 121 (FIG. 8) and 123. Tension cables 125 and 126 coupled to ends of arms 122 and 124 at an end opposite their pivot coupling to top 111 and are strung around a plurality of pulleys 127 and are coupled to the lower end 134 of control rod 128 of a cylinder 129. Cylinder 129 and pulleys 127 are mounted to the side wall 133 of frame 100. When actuated to extend rod 128 from cylinder 129, the cables 125 and 126 are tensioned to selectively close the gripping arms against tension springs 121 and 123, as shown in FIG. 4, to hold the vessel 20 in a partially submerged position and fixed against rotation (FIGS. 1, 2, 4, and 5). When in this position, the cover assembly 30 can be rotated for opening (FIGS. 1 and 4) and closing (FIGS. 2 and 5), while the gripping arms hold the vessel in place using the structure and operation now discussed.

The lift assembly 110 includes an actuator cylinder 130 (FIGS. 4-8), which is pivotally coupled at pivot coupling 131 (FIG. 8) at one end to an arm 114. Cylinder 130 includes a rod 133 which is pivotally coupled at pivot axle 135 to one end of a crank arm 132 to rotate top 40 and the integral cover assembly 30 through coupling member 106 with respect to the combustion vessel 20 when held by gripper arms 122 and 124. The axle 108 (FIG. 9) of cylindrical coupling member 106 is supported by a suitable bearing in arm 114 for allowing the cover assembly 30 and top 40 to be rotated between locked and unlocked positions by the selective actuation of cylinder 130. When unlocked, cylinder 109 is actuated for raising the top 40 and cover 30 to a loading position, as shown in FIGS. 1 and 4, after an analysis has been completed or before an initial analysis.

After being loaded with a sample and a fuse, cylinder 109 is actuated to lower top 40 and cover 30 until O-ring seal 35 (FIG. 1) seats against the inner cylindrical wall of vessel 20, while arms 122 and 124 hold the vessel. Cylinder 130 is then actuated to extend rod 133 and rotate the cover assembly 30 through crank arm 132 about $\frac{1}{16}$ of a turn, such that the mating bayonet threads engage, to a locked and sealed position. Cylinder 129 is then actuated to tension cables 125 and 126, such that arms 122 and 123 release the combustion vessel 20. Cylinder 109 is then actuated to lower arm 114 and the vessel attached thereto into the bucket 50 until O-ring seal 48 engages and seals against surface 52' of the dewar 53, thereby fluidly isolating bucket 50 from jacket 80. The tapered surface 44 (FIGS. 1-3) of lower section 42 of top 40 gradually forces excess fluid and air out of the bucket 50 as cylinder 109 lowers the top into sealing engagement with the bucket. The tapered edge 52' also serves to center the top 40 on the bucket 50. The lower end of travel of cylinder 109 (fully retracted) serves as a dead stop to provide a reproducible closing and sealing pressure. Arm 114 has an adjustable mounting to cylinder shaft 112 (FIG. 4) to select the desired sealing effect.

Figure 10:
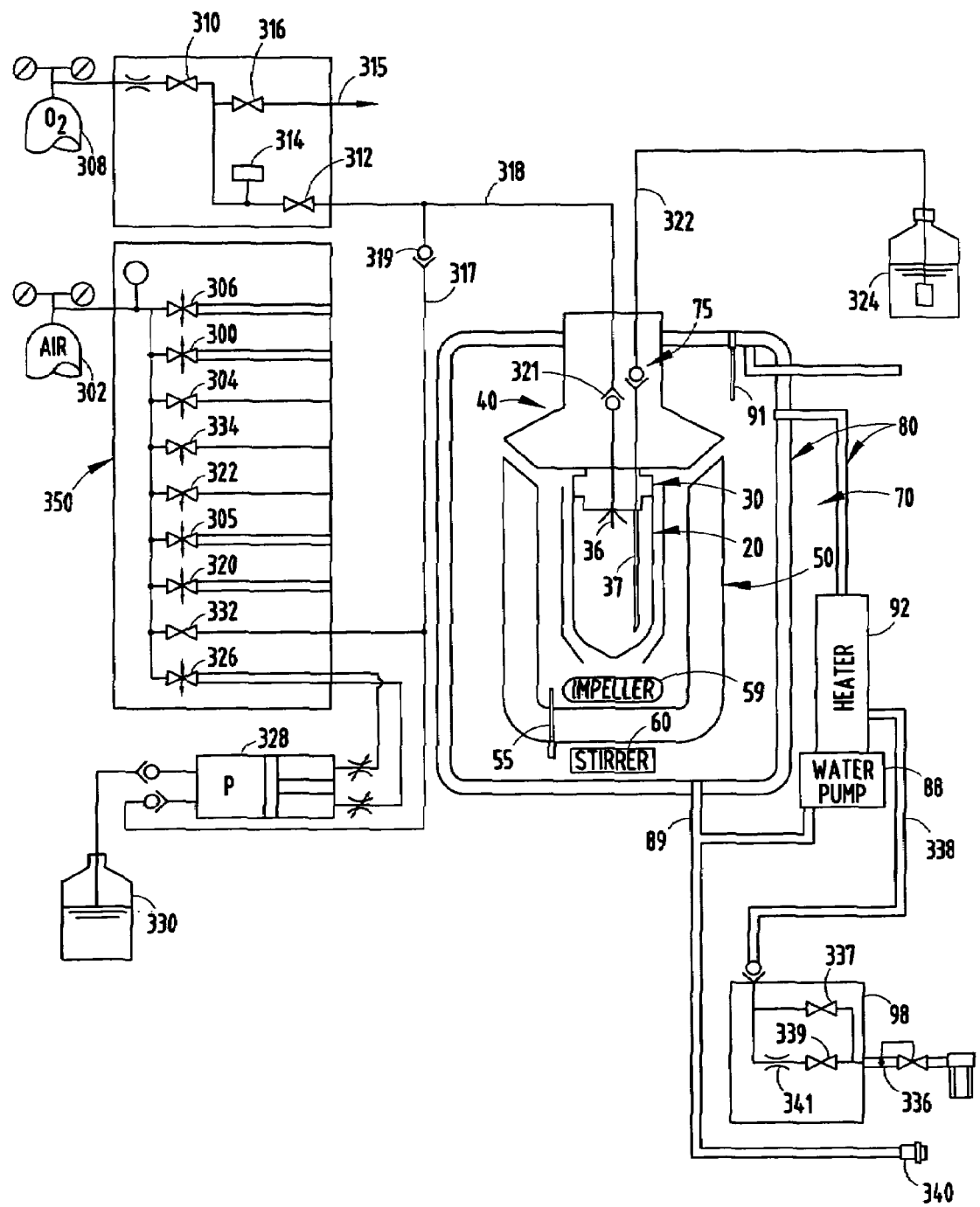
FIG. 10 is a schematic view of the calorimeter including a flow diagram of the fluid components of the calorimeter.

FIG. 10 is a schematic flow diagram of the various oxygen, air and water supplies, as well as rinse materials and control valves, conductors, and conduits, which are employed for preparing and operating the calorimeter during a cycle of analysis. The structure elements shown in the previously described drawings have the same reference numbers in FIG. 10. Referring now to FIGS. 10-12, there is shown the control system for the calorimeter which is controlled by a control circuit 140 (FIG. 12) which includes a microcontroller 142, interface circuits 144, and an Ethernet interface 146. The microcontroller is coupled to a PC 148 through Ethernet interface 146. The PC may be coupled to a monitor 149 and to a printer 150 for printing out the results of an analysis.

Figure 11A:
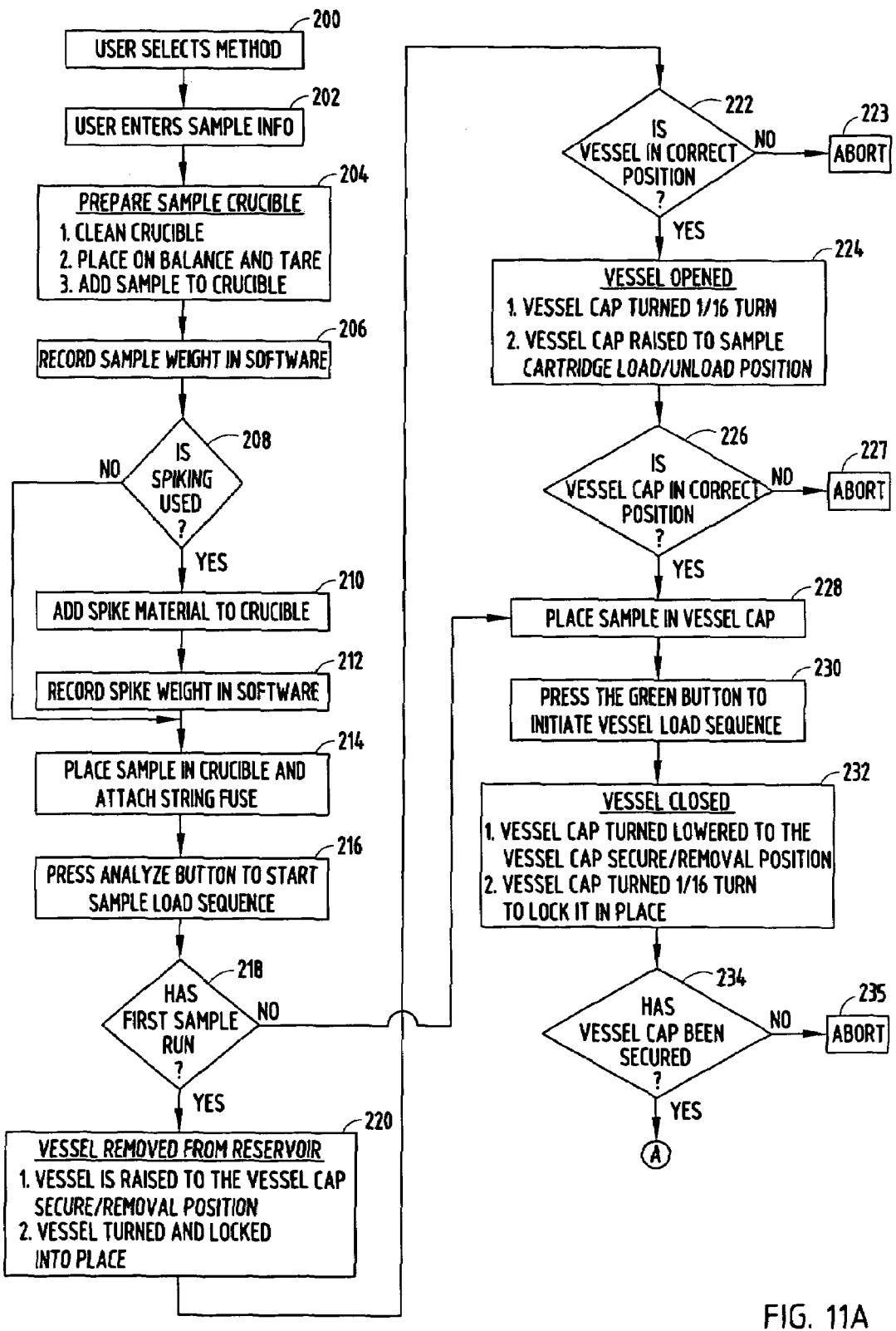
FIGS. 11A-11C are a flow diagram showing the steps in the sequence of operation of the calorimeter of the present invention.
Figure 12:
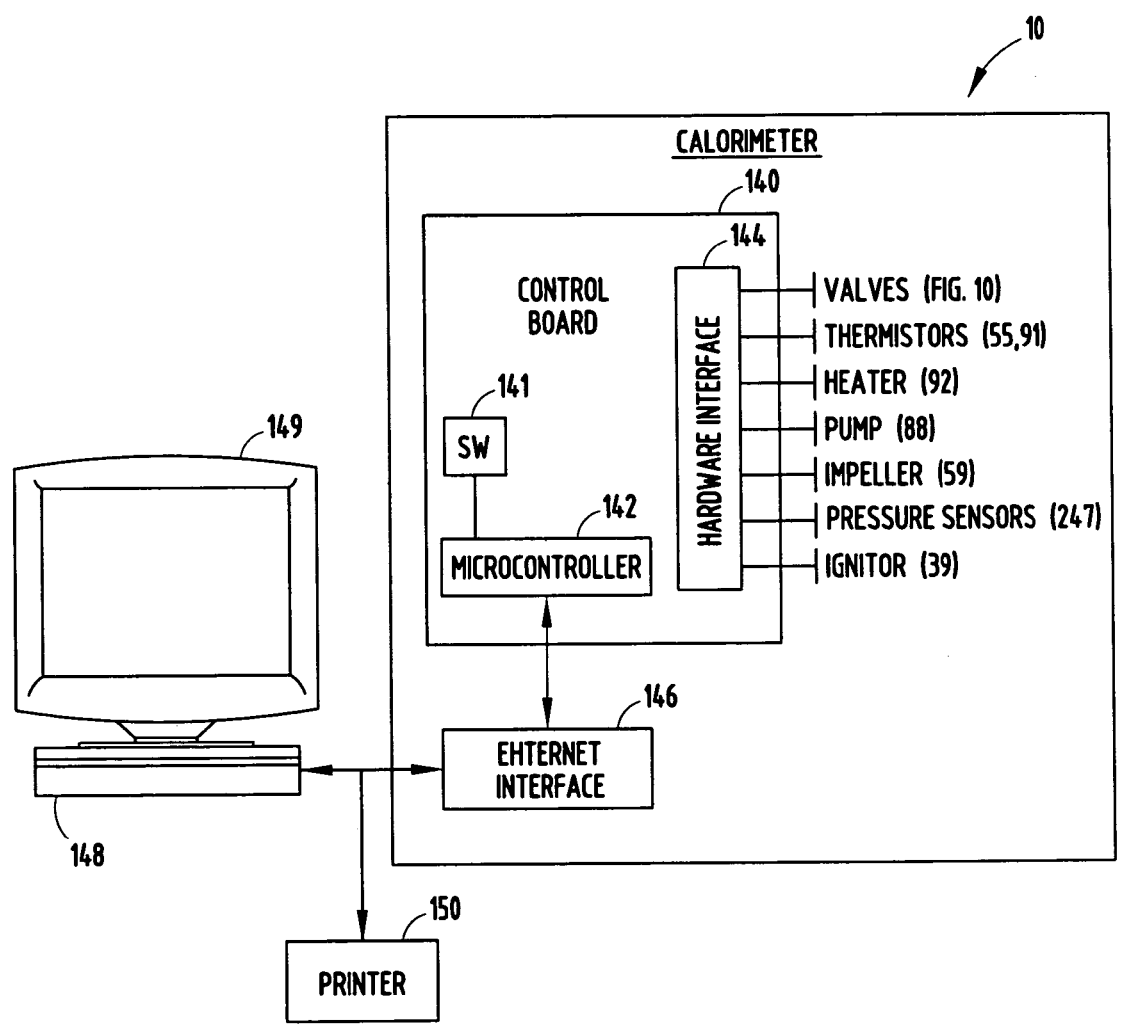
FIG. 12 is a block electrical circuit diagram of the control system for the calorimeter.

A computer 148 conventionally includes a keyboard for the operator to input parameters for the operation of an analysis, including the selection of a method as indicated by block 200 in FIG. 11A and sample information data, such as sample type, weight and the like, as shown by blocks 202 and 206. The operator then cleans the crucible, weighs the sample, and adds the sample to the crucible, as shown by block 204, recording the sample information as shown by block 206. The program then asks the operator whether or not spiking will be employed, as shown by block 208. If so, a spiking material is added to the sample, as shown by block 210, and the weight of the spiking material is added into the system as shown by block 212. If no spiking is employed, the next step is block 214 in which the sample is placed in the crucible 31, the crucible 31 is placed in the ring holder 33 (FIGS. 1 and 4), and fuse 39' is installed. From then on the sequence of operation of the calorimeter 10 is entirely automated, which automated sequence is initiated by an operator actuating a switch 141 (FIG. 12), as indicated by block 216 in the flow diagram of FIG. 11A.

With the analyzer in the position shown in FIG. 1, the vessel cover 30 is first lowered by the actuation of valve 300 (FIG. 10) which applies pneumatic pressure from a source 302 to cylinder 109 (FIG. 4) to initially lower the top 40 into engagement with vessel 20. Next, the cap lock valve 304 (FIG. 10) is actuated, which actuates cylinder 130 (FIG. 5) for locking the cap to the vessel 20. Once cap 30 has been locked to the vessel 20, valve 305 (FIG. 10) is actuated to actuate the gripper assembly 120 by activation of cylinder 129 to release the tension on cables 125 and 126, such that gripper arms 122 and 124 release the vessel from the grippers with the vessel and top still being coupled to the lift assembly 110 (FIG. 6).

Subsequently, the vessel is lowered to the position shown in FIGS. 3 and 7 within the bucket 50 by actuation of the vessel lowering valve 306 (FIG. 10), with this sequence being illustrated in FIGS. 11A and 11B as blocks 218 through 238. The water level is checked by the water level sensor 96 (FIG.

1), as indicated by block 242 (FIG. 11B), and, if the water level is acceptable, a test is made of the heating filament 39, as indicated by block 244. If the water level is low, water is introduced through manifold 98, and parts 93 and 94 and the analysis sequence is restarted once the equilibrium temperature has been reached, as indicated by block 241 in FIG. 11B. If firing element 39 for fuse 39' is open, the analysis is aborted, as indicated by block 245.

Figure 11B:
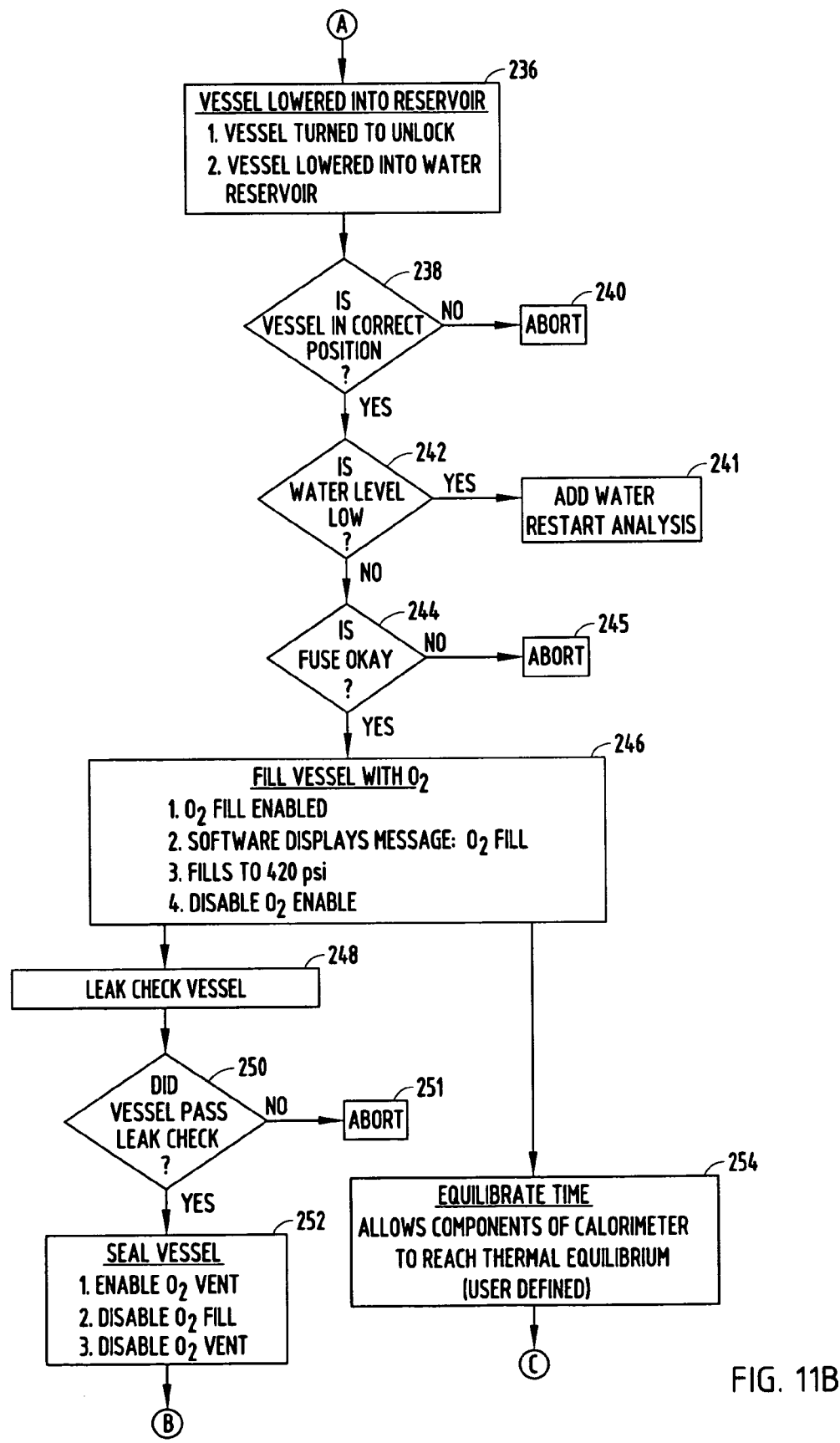

The next step is the filling of the vessel with oxygen, as indicated by block 246 in FIG. 11B, which is achieved from the supply 308 (FIG. 10) of pressurized oxygen through valves 310 and 312 with a pressure regulator 314 monitoring the oxygen pressure, which is approximately 500 psi. An oxygen vent valve 316 is employed for venting oxygen through exhaust vent 315 upon completion of filling. The oxygen flows into the analyzer through conduit 318 and through a check valve 321 within top 40 to nozzle 36.

Once the oxygen pressure in the vessel has reached 420 psi as determined by pressure sensor 247 (FIG. 12) which is located within vessel 20, oxygen valve 310 is disabled. Then, the pressure sensor is monitored to determine if the vessel has any leaks, as indicated by block 248 (FIG. 11B). If the vessel passes the leak test as indicated by block 250, valve 312 is closed and subsequently vent 316 is opened, as indicated by block 252. At the same time this takes place, the equilibration time as selected by the operator has begun as indicated by block 254 in FIG. 11B to allow the calorimeter to reach thermal equilibrium prior to the firing of the fuse 39'.

The next step is the firing of fuse 39' by the igniter 39 (indicated by block 258) in which the enriched oxygen atmosphere within the combustion vessel combusts the sample, raising the temperature within the vessel 20, which, in turn, transfers the heat to the circulated water within bucket 50. During the entire time the vessel is submerged, the water pump 88 and heater 92, in conjunction with jacket thermister 91 and water manifold 98 maintain the temperature within the jacket 80 at the 25° C. level. The temperature detected by bucket thermister 55 is then monitored, as indicated by block 260 and 262 to calculate, using standard ASTM methodology, the calorific value of the sample contained within vessel 20 using a conventional algorithm.

Figure 11C:
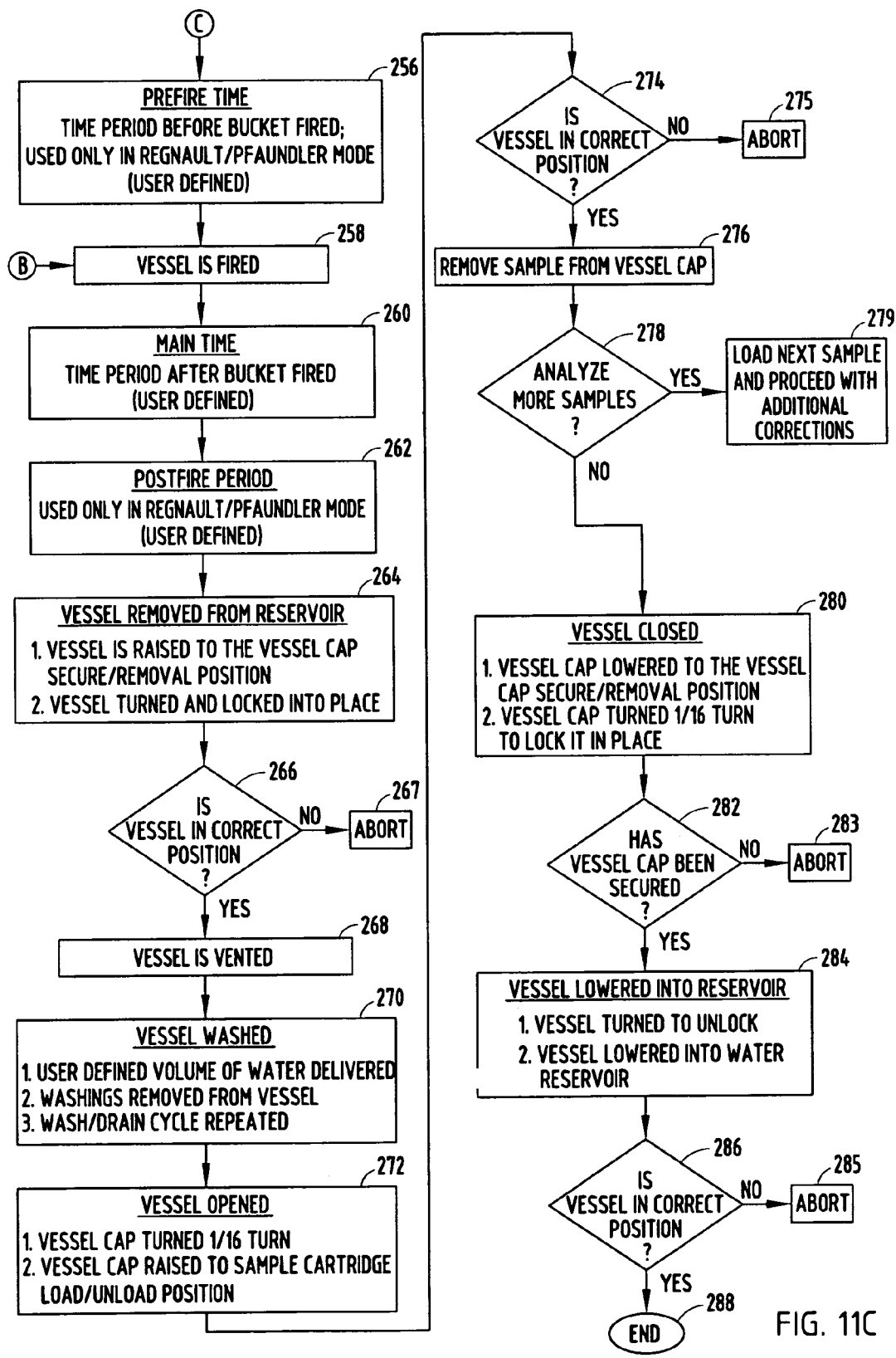

Next, the vessel raising and lower cylinder 306 is actuated to control cylinder 109 to raise the vessel to the intermediate position (shown in FIG. 5) where gripper assembly 120 is actuated through valve 320 to actuate cylinder 129 for gripping and holding the vessel in the position shown in FIG. 5, thus raising and locking the vessel in position as illustrated by block 264 and FIG. 11C. The vessel is checked for being in the proper position, as shown by step 266, by suitable sensors (not shown). Next, the vessel is vented, as illustrated by block 268. This process includes the actuation of the vessel exhaust valve 75 (FIG. 9) by the application of pneumatic pressure through valve 322 (FIG. 10), which applies pressure from inlet 79 to pneumatic cylinder 79' (FIG. 9) to actuate hammer 76 which, in turn, actuates the valve 75 venting the high pressure exhaust gases from the vessel through the outlet conduit in the Kynar® block 78 through top 40 to a vent station 324, which includes a suitable fluid and filter mechanism.

The vessel is then washed by the application of a pressure through valve 326 to a proportional pump 328, which draws cleaning fluids, such as a titration/rinse and/or water in reservoir 330 (FIG. 10) and injects the washing fluid under air pressure also from the purge valve 332 and conduits 317 and 318 through valves 319 and 320 into vessel 20 through nozzle 36. The pneumatic pressure and cleaning fluid provided by pump 328 and air from cylinder 302 substantially flushes the byproducts of combustion from the vessel and up through sipper tube 37 through valve 75 into the exhaust collector vessel 324. This cycle is repeated as necessary, as indicated by block 270 in FIG. 11C.

Next, valve 334 in the valve manifold 350 shown in FIG. 10 is actuated to actuate cylinder 130 to unlock the top 40 from the vessel 20 by rotating the top in a counterclockwise direction ⅟₁₆ of a turn, as indicated by block 272 in FIG. 11C. Subsequent to rotation of top 40 to unlock the top, valve 306 is again actuated to actuate cylinder 109 to raise the top and cover 30 from the vessel to the initial position shown in FIG. 4. These steps are represented by block 272 in FIG. 11C. The position of the vessel is then checked, as indicated by block 274, and the crucible 31 is removed from the vessel cover 32 as indicated by block 276. The program then asks whether additional samples are to be run, as indicated by block 278. If not, the vessel is again closed, as shown by block 285 in the previously described sequence. If additional samples are to be run, the operator proceeds to step 200 in FIG. 11A. If no additional samples are to be run, the vessel is lowered into the reservoir, as indicated by block 284, through the sequence previously described, is position tested as indicated by block 286, and the program ended, as indicated by block 288.

Prior and during an analysis, the water manifold 98 (FIG. 10) receives fresh water from a water fill inlet 336, which is cooler than the 25° C. water as necessary, and introduces this cooling water to the heater 92 through conduit 338 to add water as required to the jacket 80 if either the water level is low, as detected by sensor 96, or the water temperature is too high with heater 92 turned off. Thus, the temperature can be increased or decreased with the system shown by the introduction of either tap water or water from a chiller through inlet 336 and valves 337 and 339 as desired. Valve 337 provides a quick fill or quick cool higher flow rate, while a restricter 341 limits the filling flow rate. The jacket can be emptied through a drain fitting 340, which has a quick disconnect which seals the drain during normal operation of the calorimeter.

Thus, the calorimeter system of the present invention provides a hands-off automated handling of the calorimeter vessel 20 within a isothermal reservoir 70 which has a dividing member comprising the top 40 and seal 48 which divides bucket 50 from the jacket 80 and provides a carefully controlled environment for the detection of the temperature increase within the bucket during an analysis. The jacket temperature is carefully controlled through the use of a circulatory system including a heater and cooled water inlets to maintain the jacket temperature substantially stable at 25° C. Further, the system of the present invention provides a unique automated washing system for the vessel, such that physical operator intervention is unnecessary, thereby increasing the reliability and repeatability of subsequent analyses.

It will become apparent to those skilled in the art that various modifications to the preferred embodiment of the invention as described herein can be made without departing from the spirit or scope of the invention as defined by the appended claims.

The invention claimed is:

1. A calorimeter system including an isothermal reservoir comprising:
   a combustion vessel;
   an outer jacket having a fluid inlet and an outlet located near an opposite end of said inlet;
   a heater and a pump associated with said jacket for circulating fluid from said fluid outlet through said heater to said inlet provide a constant temperature of fluid within said jacket;

a thermally insulated member positioned within said jacket and having an internal volume therein defining a bucket for receiving a calorimeter combustion vessel, said insulating member having a wall with a height less than the height of said jacket such that fluid in said jacket fills said bucket over said wall;

a cover for enclosing said combustion vessel; and a movable closure member including a seal engaging said insulated member for selectively sealing said bucket from said jacket when in a first position during combustion of a sample within said combustion vessel and movable to a second position spaced from said insulated member to allow water from said jacket to enter said bucket only over said wall.

2. The system as defined in claim 1 wherein said bucket includes a baffle and a floor having an impeller for circulating fluid around said combustion vessel within said bucket on opposite sides of said baffle for homogenizing the temperature of the fluid contained within said bucket.

3. The system as defined in claim 2 wherein said jacket includes upper fluid inlets coupled to a discharge end of said pump, wherein one inlet is directed toward said jacket volume surrounding said insulated member and another inlet is directed to the area above an upper end of said insulated member to introduce fluid into said bucket for quickly homogenizing the fluid temperature within said bucket and jacket.

4. The system as defined in claim 3 wherein said insulated member comprises a generally cylindrical member, wherein the upper end of said member includes an inclined annular edge which engages said seal of said movable member for centering and sealing said member to said bucket when said combustion vessel is introduced into said bucket.

5. The system as defined in claim 4 wherein said impeller includes magnetic poles mounted therein and wherein said jacket further includes a rotating magnetic field generator for rotating said impeller.

6. The system as defined in claim 5 wherein said jacket includes a temperature detecting member and wherein said system further includes a control circuit coupled to said temperature detecting member and to said heater for controlling the temperature of the fluid within said jacket and said bucket.

7. The system as defined in claim 6 wherein said system further includes a measurement temperature sensor positioned within said bucket for detecting the temperature of the fluid surrounding said combustion vessel prior to and after combustion of a sample.

8. A calorimeter including a combustion vessel and an isothermal reservoir for receiving said combustion vessel comprising:

a combustion vessel with an open top;

a closure member for said top of said combustion vessel, wherein said combustion vessel and closure member include interlocking members;

a lifting arm coupled to said cover for said combustion vessel for lifting said combustion vessel and said cover when said combustion vessel and cover are locked together;

a gripper assembly including arms for engaging said combustion vessel when raised from an isothermal reservoir for holding the combustion vessel in a fixed vertical position and against rotation;

rotary actuator means coupled to said cover of said combustion vessel for rotating said cover while said arms of said gripper assembly hold said vessel in a stationary position to disengage the locking members between said cover and said combustion vessel; and wherein said lifting arm subsequently raises the cover from said combustion vessel for access thereto.

9. The calorimeter as defined in claim 8 including an outer jacket having a wall and an upper end and a lower end, said jacket including a fluid inlet near the lower end for coupling to a supply of fluid, said jacket further including a lower fluid outlet at said lower end and an overflow outlet located near said upper end;

a bypass flow path coupled between said lower end of said jacket and said upper end, said bypass flow path including a heater and a pump for circulating fluid from said fluid inlet and said lower fluid outlet though said heater to an upper end of said jacket;

a thermally insulated member positioned within said jacket in spaced relationship to the wall thereof and having an internal volume therein defining a bucket for receiving a calorimeter combustion vessel, said insulating member having a height less than the height of said jacket such that fluid in said jacket fills said bucket; and a movable closure member selectively coupled to said calorimeter combustion vessel and including a seal engaging said insulated member for sealing said bucket from said jacket during combustion of a sample within said combustion vessel.

10. The calorimeter as defined in claim 9 wherein said bucket includes a baffle and a floor having an impeller for circulating fluid around said combustion chamber within said bucket on opposite sides of said baffle for homogenizing the temperature of the fluid contained within said bucket.

11. The calorimeter as defined in claim 10 wherein said jacket includes upper fluid inlets coupled to a discharge end of said bypass flow path, wherein one inlet is directed toward said jacket volume surrounding said insulated member and another inlet is directed to the area above an upper end of said insulated member to introduce fluid into said bucket.

12. The calorimeter as defined in claim 11 wherein said insulated member comprises a generally cylindrical member, wherein the upper end of said member includes an inclined annular edge which engages said seal of said movable member for centering and sealing said closure member to said bucket when said combustion vessel is introduced into said bucket.

13. The calorimeter as defined in claim 12 wherein said impeller includes magnetic poles mounted therein and wherein said jacket further includes a rotating magnetic field generator for coupling to said impeller for rotation thereof.

14. The calorimeter as defined in claim 13 wherein said jacket includes a temperature detecting member and wherein said system further includes a control circuit coupled to said temperature sensing member and to said heater for controlling the temperature of the fluid within said jacket and within said bucket.

15. The calorimeter as defined in claim 14 wherein said system further includes a measurement temperature sensor positioned within said bucket for detecting the temperature of the fluid surrounding said combustion vessel prior to and after combustion of a sample.

16. A fully automated calorimeter including a combustion vessel and an isothermal reservoir for receiving said combustion vessel comprising:

a combustion vessel with an open top;

a cover for said top of said combustion vessel, wherein said combustion vessel and closure member include interlocking members;

an isothermal reservoir including a bucket for receiving said combustion vessel and a surrounding water jacket having water therein controlled to a predetermined temperature;

a lift arm coupled to said cover for said combustion vessel for lifting said combustion vessel and said cover when said combustion vessel and cover are locked together to a first position in which an upper end of said combustion vessel and said cover are withdrawn from said bucket with a lower end of said combustion vessel held in thermal contact with said water jacket;

a gripper assembly including arms for engaging said combustion vessel when in said first position for holding the combustion vessel in said first position and against rotation;

rotary actuator means coupled between said lift arm and said cover of said combustion vessel for rotating said cover while said arms of said gripper assembly hold said vessel in a stationary position to disengage the locking members between said cover and said combustion vessel; and said arm is movable to subsequently raise the cover from said combustion vessel to a second position for gaining access thereto and a third lowered position when said cover is locked on said vessel for sealing a portion of said isothermal reservoir surrounding said combustion vessel from the remainder of said isothermal reservoir during combustion of a sample.

17. The calorimeter as defined in claim 16 wherein said isothermal reservoir includes an outer jacket having a wall and an upper end and a lower end, said jacket including a fluid inlet near the lower end for coupling to a supply of fluid, said jacket further including a lower fluid outlet at said lower end and an overflow outlet located near said upper end;

a bypass flow path coupled between said lower end of said jacket and said upper end, said bypass flow path including a heater and a pump for circulating fluid from said fluid inlet and said lower fluid outlet through said heater to an upper end of said jacket;

a thermally insulated member positioned within said jacket in spaced relationship to the wall thereof and having an internal volume therein defining a bucket for receiving said combustion vessel, said insulating member having a height less than the height of said jacket such that fluid in said jacket fills said bucket; and said cover for said combustion vessel including a seal engaging said insulated member for sealing said bucket from said jacket during combustion of a sample within said combustion vessel.

18. A calorimeter system including an isothermal reservoir comprising:

a combustion vessel having an open top and a cover for selectively enclosing said combustion vessel;

an outer jacket having a jacket wall and an upper end and a lower end, said jacket including a fluid inlet near the lower end for coupling to a supply of fluid, said jacket further including a lower fluid outlet at said lower end and an overflow outlet located near said upper end;

a bypass flow path coupled between said lower end of said jacket and said upper end, said bypass flow path including a heater and a pump for circulating fluid from said fluid inlet and said lower fluid outlet through said heater to an upper end of said jacket;

a thermally insulated member positioned within said jacket in spaced relationship to said jacket wall thereof and having an internal volume therein defining a bucket for receiving a calorimeter combustion vessel, said insulating member having a wall with a top below the upper end of said jacket wall such that fluid in said jacket fills said bucket; and a movable closure member selectively coupled to said calorimeter combustion vessel and including a seal engaging said insulated member for sealing said bucket from said jacket when in a first position during combustion of a sample within said combustion vessel, said closure member movable to a second position above said insulated member to allow water from said jacket to spill over said top of said wall of said insulated member.

19. The system as defined in claim 18 wherein said bucket includes a baffle and a floor having an impeller for circulating fluid around said combustion chamber within said bucket on opposite sides of said baffle for homogenizing the temperature of the fluid contained within said bucket.

20. The system as defined in claim 19 wherein said jacket includes a pair of upper fluid inlets coupled to a discharge end of said bypass flow path, wherein one inlet is directed toward said jacket volume surrounding said insulated member and another inlet is directed to the area above an upper end of said insulated member to introduce fluid into said bucket.

21. The system as defined in claim 20 wherein said insulated member comprises a generally cylindrical vacuum dewar, wherein the upper end of said vacuum dewar includes an inclined annular edge which engages said seal of said movable member for sealing said bucket when said combustion vessel is introduced into said bucket.

22. The system as defined in claim 19 wherein said impeller is made of a nonferrous material and includes magnetic poles mounted therein and wherein said jacket further includes a rotating magnetic field generator for coupling to said impeller for rotation thereof.

23. The system as defined in claim 18 wherein said jacket includes a temperature detecting member and wherein said system further includes a control circuit coupled to said temperature detecting member and to said heater for controlling the temperature of the fluid within said jacket and said bucket.

24. The system as defined in claim 23 wherein said system further includes a measurement temperature sensor positioned within said bucket for detecting the temperature of the fluid surrounding said combustion vessel prior to and after combustion of a sample.

25. A calorimeter system including an isothermal reservoir comprising:

a combustion vessel having an open top and a cover for selectively enclosing said combustion vessel;

an outer jacket having a jacket wall and an upper end and a lower end, said jacket including a fluid inlet near the lower end for coupling to a supply of fluid, said jacket further including a lower fluid outlet at said lower end and an overflow outlet located near said upper end;

a bypass flow path coupled between said lower end of said jacket and said upper end, said bypass flow path including a heater and a pump for circulating fluid from said fluid inlet and said lower fluid outlet through said heater to an upper end of said jacket;

a thermally insulated member positioned within said jacket in spaced relationship to said jacket wall thereof and having an internal volume therein defining a bucket for receiving a calorimeter combustion vessel, said insulating member having a wall with a top below the upper end of said jacket wall such that fluid in said jacket fills said bucket;

a movable closure member coupled to said cover of said calorimeter combustion vessel and including a seal engaging said insulated member for sealing said bucket from said jacket when in a first position during combustion of a sample within said combustion vessel, said closure member movable to a second position above said insulated member lifting said combustion vessel at least partially from said bucket to allow water from said jacket to spill over said top of said wall of said insulated member into said bucket; and a lift assembly coupled to said closure member for moving said closure member between said first and second positions.

* * * * *